United States Patent [19]

Nakanishi et al.

[11] Patent Number: 5,518,398
[45] Date of Patent: May 21, 1996

[54] DENTAL HANDPIECE HAVING ROTATABLE CONTACT MEMBER

[75] Inventors: Eiichi Nakanishi; Sosaku Kawata; Yuichi Shibata, all of Kanuma, Japan

[73] Assignee: Nakanishi Dental Mgf. Co., Ltd., Kanuma, Japan

[21] Appl. No.: 291,271

[22] Filed: Aug. 16, 1994

[30] Foreign Application Priority Data

Aug. 20, 1993 [JP] Japan ................ 5-045460 U

[51] Int. Cl.⁶ ....................................... A61C 1/14
[52] U.S. Cl. ................ 433/127; 433/128; 433/129
[58] Field of Search ..................... 433/127, 128, 433/129

[56] References Cited

U.S. PATENT DOCUMENTS 4,773,856  9/1988  Mosimann ............... 433/127
4,781,589  11/1988 Bareth ..................... 433/127
4,940,410  7/1990  Apap et al. ............. 433/127 X
5,028,181  7/1991  Jenkins et al. ......... 433/128 X

FOREIGN PATENT DOCUMENTS 0505888  9/1992  European Pat. Off. ...... 433/127
599782   5/1978  Switzerland ............... 433/127

Primary Examiner—Nicholas D. Lucchesi
Attorney, Agent, or Firm—Malcolm B. Wittenberg

[57] ABSTRACT

A dental handpiece contains a tool for dental treatment operation, tool holding members for detachably and rotatably holding the tool, tool detachment members for abutting against the tool holding members to detach the tool from the tool holding members, and rotatable contact members capable of being point-contacted with the tool holding members. The rotatable contact members when contacted with the tool holding members is rotatable with the tool holding members.

3 Claims, 5 Drawing Sheets

DENTAL HANDPIECE HAVING ROTATABLE CONTACT MEMBER

BACKGROUND OF THE INVENTION

This invention relates to a dental handpiece on which a tool for dental treatment can be mounted detachably. More particularly, it relates to a dental handpiece having a rotatable contact member capable of preventing mechanical or thermal injuries otherwise caused by mistaken detachment operation of the dental treatment tool mounted thereon.

Up to now, a dental handpiece having a dental treatment tool mounted thereon has been used extensively for dental treatment. Such conventional dental handpiece is now explained by referring to FIG. 4.

FIG. 4 shows the distal end part of a conventional dental handpiece 40 which is made up of a head casing 41 for mounting a dental treatment tool 9 thereon and a head cap 42 threadedly attached to an upper part of the head casing 41.

Within the interior of the head casing 41, there is detachably mounted an inner casing 54 made up of a cartridge casing 54a and a casing cap 54b. The cartridge casing 54a has various components for holding and rotating the dental treatment tool 9 as later explained. Within the inner casing 54, there are arranged a rotary shaft 44 having a collet 43 detachably holding the dental treatment tool 9 and ball bearings 45, 46 for rotatably supporting the rotary shaft 44.

The collet 43 has plural axially extending slits 43a to permit the inner periphery at its lower end to be enlarged in diameter. The outer periphery of the collet 43 presents a tapered surface 55, the diameter of which is progressively increased towards the lower side. The collet 43 has its upper end projected above the rotary shaft 44 and formed with female screw threads. A spring 47 is placed around the outer periphery of the upper end of the collet 43. The upper tapped end of the collet 43 is engaged with a flange 49 having male screw threads 48.

The rotary shaft 44 is tubular and is formed at its lower end with a tool receiving opening 44a for receiving the dental treatment tool 9 therein. A rotor 44b in the form of an impeller is mounted on the outer periphery of the rotary shaft 44 for rotationally driving the rotary shaft 44. The rotary shaft 44 has its inner surface formed as a tapered surface 55 shaped for mating with the outer periphery of the collet 44. By such tapered inner peripheral surface of the rotary shaft 44, the collet 43 biased by the spring 47 in an upper direction, is pressed and held by the rotary shaft 44.

The ball bearings 45, 46 are arranged at the upper and lower portions of the rotary shaft 44, and are engaged with and retained by the head casing 41 and the head cap 42 via dampers 50, 51, respectively.

The head cap 42 is threadedly engaged with an upper part of the head casing 41 and has at its mid portion a pushbutton 52 for attachment and detachment of the dental treatment tool 9 held by the collet 43. The pushbutton 52 also has an engagement portion 52a capable of being engaged with a mating engagement portion 42a of the head cap 42. The pushbutton 52 has at its lower surface a spring 53 for upwardly biasing the pushbutton 52.

With the above-described dental handpiece 40, the rotor 44b provided on the rotary shaft 44 runs the dental treatment tool 9 held by the collet 43 in rotation by compressed air supplied from an air supply conduit, not shown.

For detachment of the dental treatment tool 9 from the dental handpiece 40, the pushbutton 52 is pressed down for lowering the collet 43 in order to permit the lower tapered surface 55 of the collet 43 to be enlarged so as to assure facilitated detachment of the dental treatment tool 9.

However, with such detachment mechanism of the conventional dental handpiece 40, the pushbutton 52 may be contacted with the flange 49 during the operation of the dental treatment tool 9, even if the pushbutton 52 is not pressed down so strongly as to extract the dental treatment tool 9. Thus, it may occur that, during treatment of a molar, above all, cutting of a narrow side portion, or preparation of a tooth base for a crown or a bridge, the pushbutton 52 may be caused to bear against some portion in the oral cavity, thereby inadvertently thrusting the pushbutton 52 downwards.

At this time, the pushbutton 52 thus thrust inadvertently tends to be contacted with the rotating flange 49, thus generating frictional heat and instantaneously producing a high temperature and hence an extremely dangerous state.

SUMMARY OF THE INVENTION

In view of the above-described status of the art, it is an object of the present invention to provide a dental handpiece in which it is possible to prevent generation of the frictional heat due to contact with the rotating member of the pushbutton inadvertently thrust in detaching the dental treatment tool and to prevent consequent mechanical or thermal injuries and which consequently may be used in safety.

The above and other objects of the present invention will become apparent from the following description.

According to the present invention, there is provided a dental handpiece comprising a tool for dental treatment operation, tool holding means for detachably and rotatably holding the tool, tool detachment means for abutting against the tool holding means to detach the tool from the tool holding means, and rotatable contact means capable of being point-contacted with the tool holding means, the rotatable contact means when contacted with the tool holding means being rotatable with the tool holding means.

PREFERRED EMBODIMENTS OF THE INVENTION

Figure 1A:
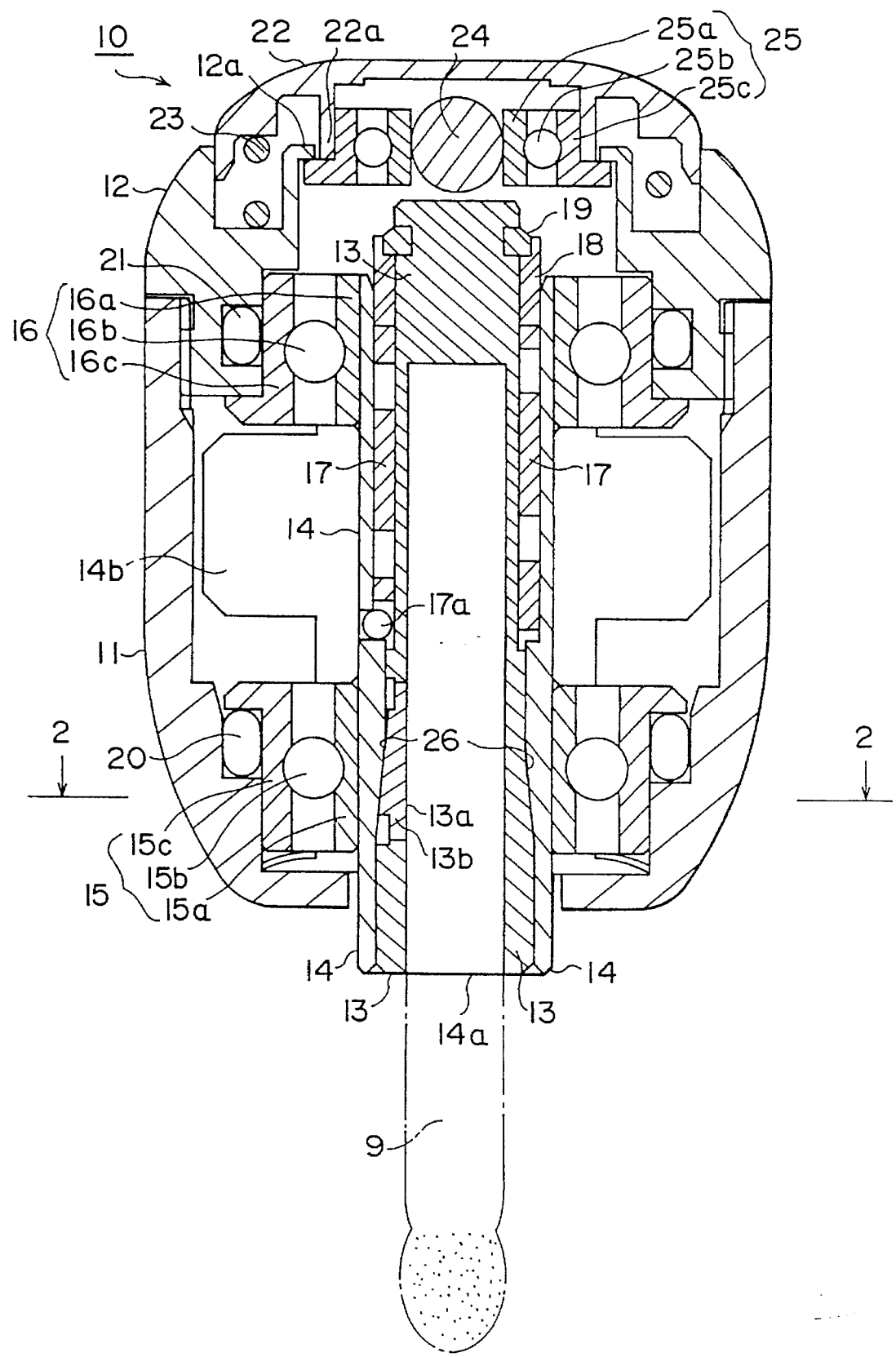
FIG. 1a is a longitudinal cross-sectional view showing a distal portion of a dental handpiece according to an embodiment of the present invention.

FIG. 1a shows a distal end portion of a dental handpiece 10. The dental handpiece 10 is made up of a head casing 11 holding a dental treatment tool 9 therein and having a variety of component parts for rotationally driving the dental treatment tool 9, as later explained, and a head cap 12 having a detachment mechanism for the dental treatment tool 9 held within the head casing 11.

Within the head casing 11, there are arranged a rotary shaft 14 having a collet 13 detachably holding the dental treatment tool 9 and ball bearings 15, 16 for rotatably supporting the rotary shaft 14.

Figure 1B:
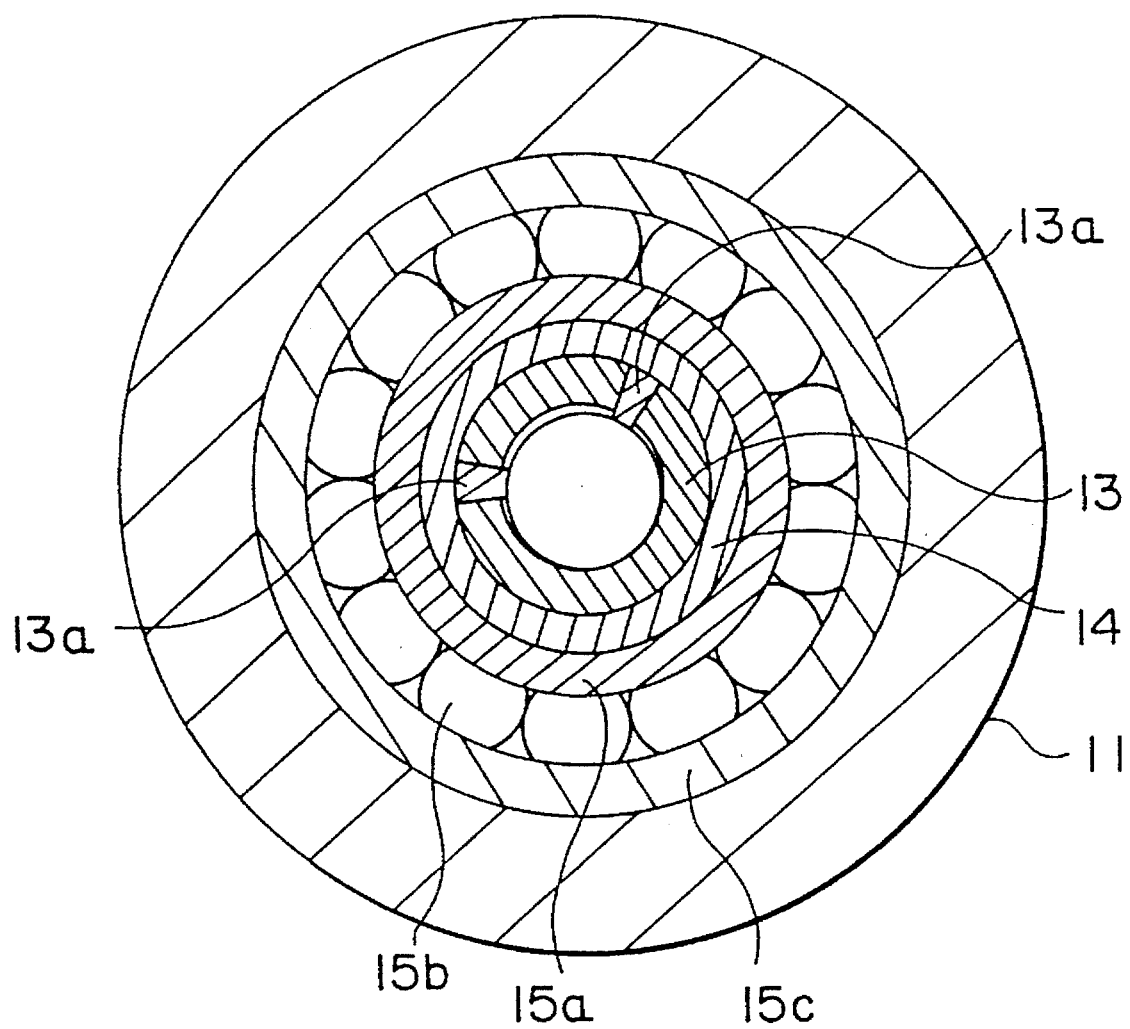
FIG. 1b is a transverse cross-sectional view taken along line 2—2 of FIG. 1.

The outer peripheral surface of the collet 13 has a tapered surface 26, the diameter of which is gradually increased downwards. The tapered surface 26 has two grooves 13a opened in the inner surface of the collet at an angular distance of 120° from each other in the circumferential direction as shown in FIG. 1b. Within each of these grooves 13a, there is mounted a chuck piece 13b which is projected slightly inwards from the plane of the inner radius of the collet 13 when the collet 13 is mounted within the inside of the rotary shaft 14.

The rotary shaft 14 is tubular and presents at its lower end a tool receiving opening 14a for receiving the dental treatment tool 9 therein. On the outer periphery of the rotary shaft 14 is mounted a rotor 14b in the form of an impeller for rotationally driving the rotary shaft 14. The inner periphery of the rotary shaft 14 presents a tapered surface 26 mating with the outer periphery of the collet 13. In an upper portion of the rotary shaft 14, there are arranged, around the inner periphery of the rotary shaft 14, a spring 17 for holding the collet 13 toward upward direction, a spring retainer 18 for the spring 17 and a positioning ball 17a acting simultaneously as rotation stop means. By securing the spring retainer 18 by a fastener member 19 to an upper portion of the collet 13, the collet may be biased upwards so as to be held within the interior of the rotary shaft 14.

The ball bearings 15, 16 are arranged at an upper portion and at a lower portion of the rotary shaft 14 for stably and rotatably supporting the rotary shaft 14. The lower ball bearing 15 has plural balls 15b interposed between an inner race 15a secured to the rotary shaft 14 and an outer race 15c retained by the head casing 11 via a vibration damper 20 for rotatably supporting the lower portion of the rotary shaft 14. The upper ball bearing 16 has plural balls 16b interposed between an inner race 16a secured to the rotary shaft 14 and an outer race 16c retained by the head cap 12 via a vibration damper 21 for rotatably supporting the upper portion of the rotary shaft 14. The head cap 12 is threadedly engaged with the upper portion of the head casing 11 and has at its mid portion a pushbutton 22 for detachment of the dental treatment tool 9 held by the collet 13. Below the pushbutton 22 there are arranged a spring 23 for upwardly biasing the pushbutton 22, a ball-shaped contact member 24 for contacting with the upper end of the collet 13 when the pushbutton 22 is thrust downwards against the bias of the spring 23, and a ball bearing 25 for rotatably supporting the contact member 24. The ball bearing 25 has an inner race 25a secured to the contact member 24 and an outer race 25c mounted on an outer race attachment 22a of the pushbutton 22 via plural balls 25b. The outer race 25c is retained by a retainer 12a of the head cap 12 in order to hold the pushbutton 22 biased by the spring 23 at a pre-set position.

Figure 2:
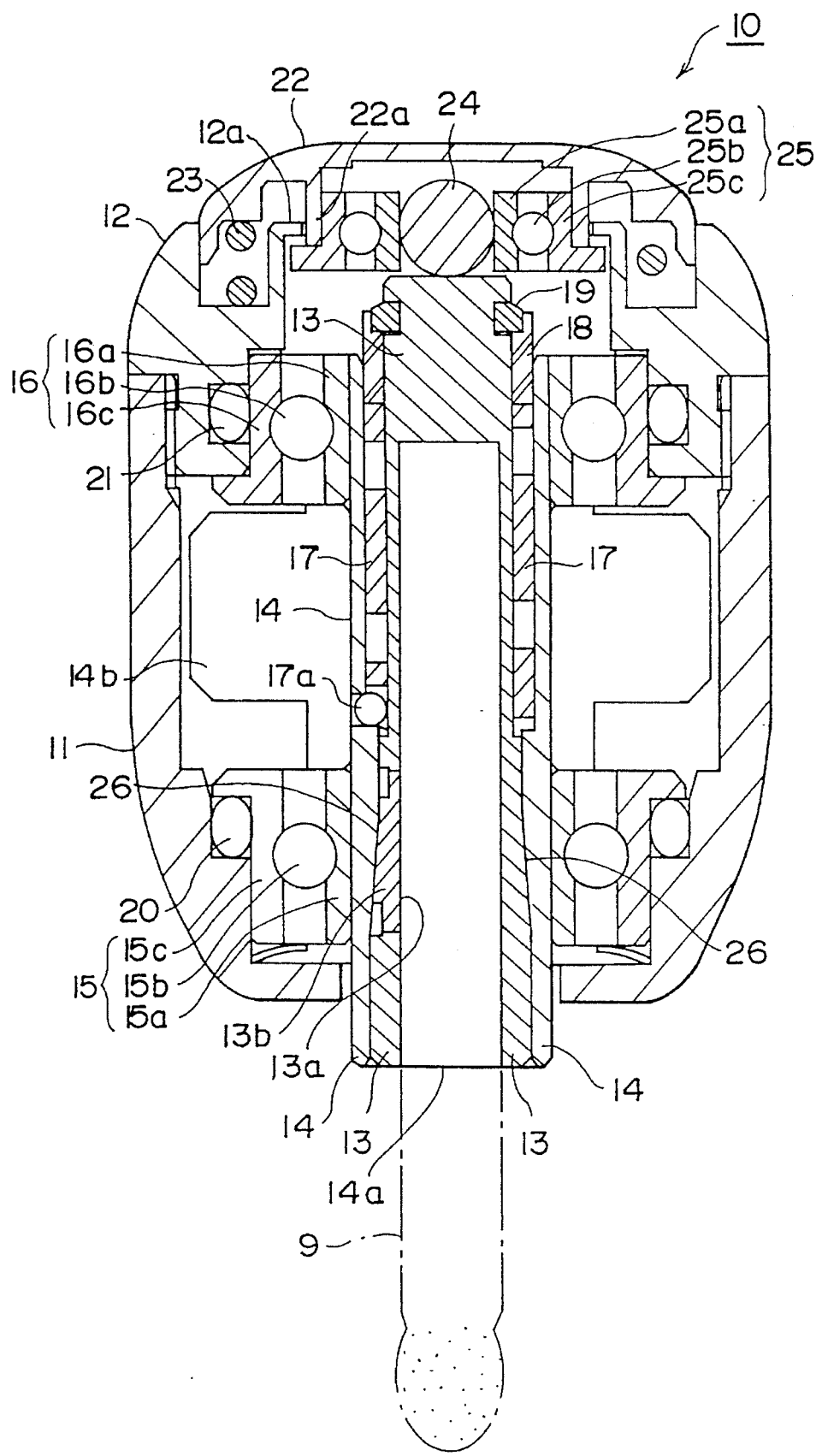
FIG. 2 is a longitudinal cross-sectional view showing the pushbutton of FIG. 1a in the state of being pressed down.

If, with the above-described dental handpiece 10, the pushbutton 22 is thrust downwards, as shown in FIG. 2, the contact member 24 provided below the pushbuttton 22 is contacted with the upper end of the collet 13 and is rotated in unison with the rotating collet 13. Consequently, even if the pushbutton 22 is thrust downwards inadvertently, the dental handpiece 10 may be prevented from being injured thermally or mechanically.

Figure 3:
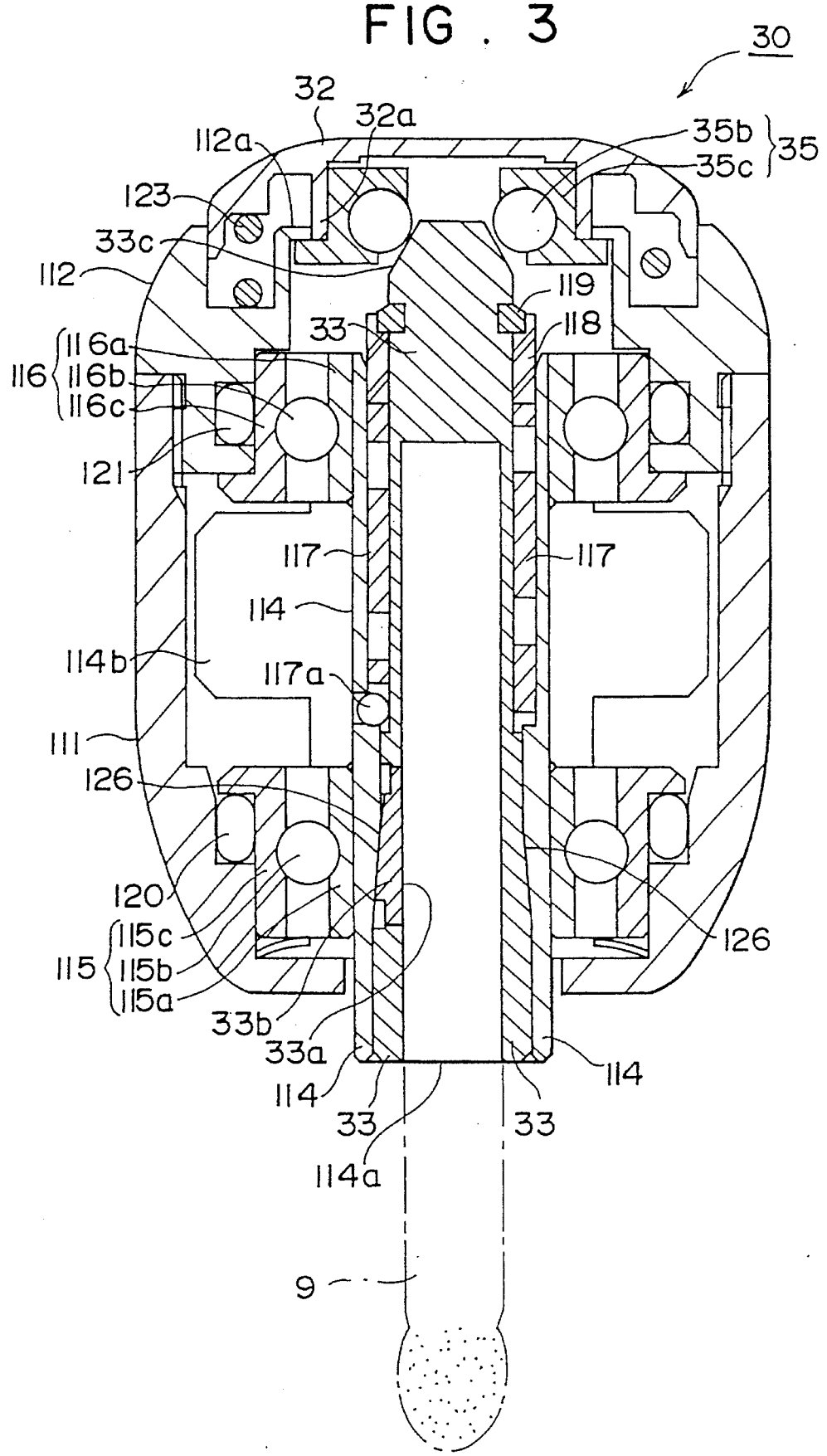
FIG. 3 is a longitudinal cross-sectional view showing a distal portion of a dental handpiece according to another embodiment of the present invention.
Figure 4:
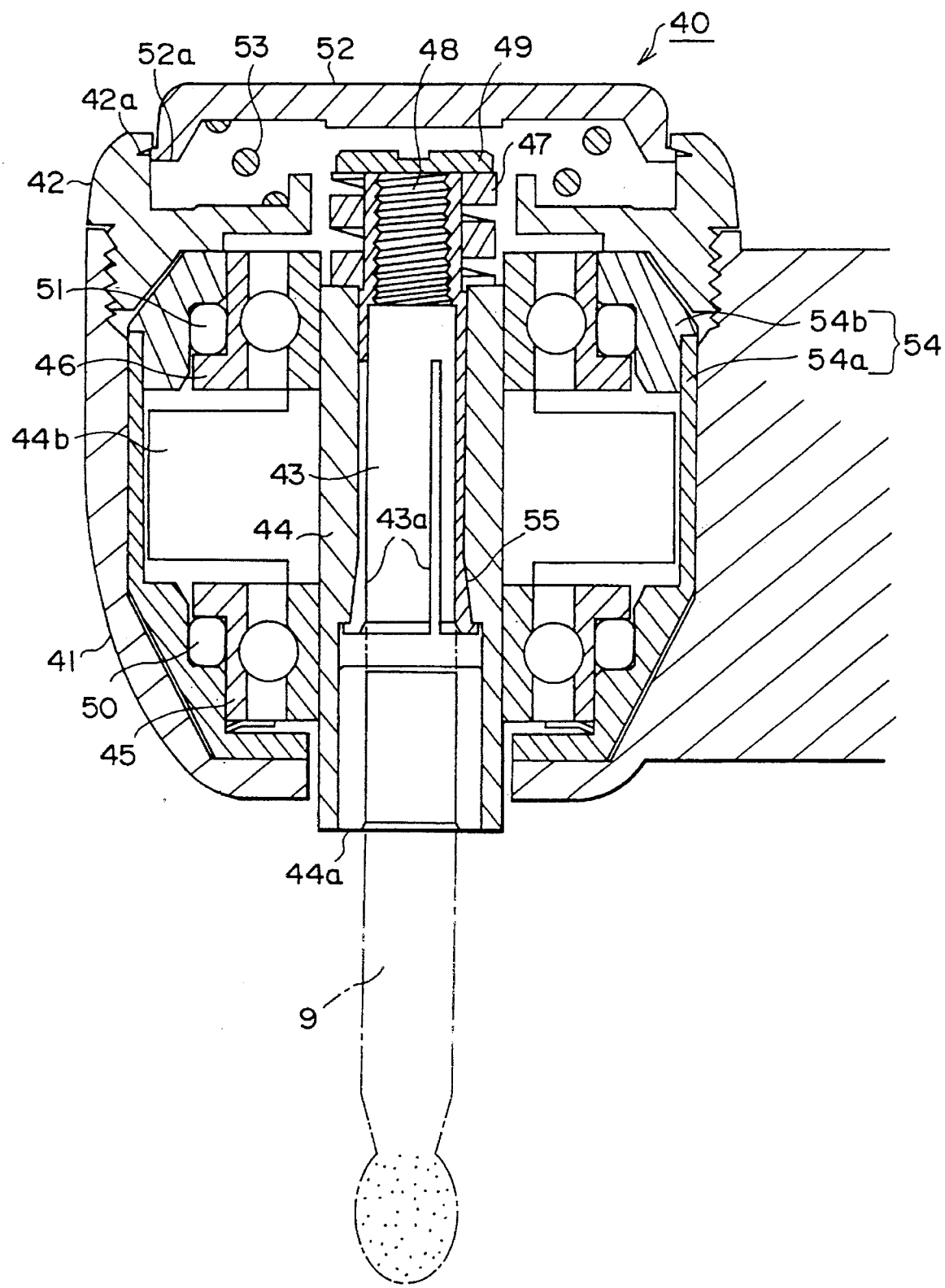
FIG. 4 is a longitudinal cross-sectional view showing a conventional dental handpiece.

Referring to FIG. 3, a modification of the present invention will be explained in detail.

In FIG. 3, there is shown a dental handpiece 30 which, similarly to the dental handpiece 10, is made up of a head casing 111 including a variety of component parts for holding and rotationally driving a dental treatment tool 9 and a head cap 112 having a detachment mechanism for the dental treatment tool 9 held within the head casing 111.

With the present dental handpiece 30, the pushbutton 32 and the collet 33 making up the detachment mechanism for the dental treatment tool 9 of the dental handpiece 10 are modified in a manner to be now explained. Since the remaining components are the same as those of the previously explained dental handpiece 10 shown in FIG. 1, these common components are indicated by the same numerals as those of the previous embodiment added by 100 and any redundant explanation is omitted for simplicity.

Similarly to the above-described collet 13, the collet 33 of the dental handpiece 30 has its outer periphery designed as a tapered surface 126, the diameter of which is progressively increased downwards. The tapered surface 126 has two grooves 33a opened in the inner surface of the collet at an angular distance of 120° from each other along its circumference. Within each of these grooves 33a, there is mounted a chuck piece 33b which is projected slightly inwards from the plane of the inner radius of the collet 33 when the collet 33 is mounted within the inside of the rotary shaft 114. The upper end of the collet 33 is formed as a contact potion 33c contacted by a contact member 35 with the pushbutton 22.

The lower portion of the pushbutton 32 for detachment of the dental treatment tool 9 is associated with a spring 123 for biasing the pushbutton 32 upwards and the contact member 35 adapted for being contacted with the upper end of the collet 33. The contact member 35 is comprised of balls 35b and an outer race 35c as a pivot bearing for rotatably holding the balls 35b. The outer race 35c is mounted on an outer race mounting portion 32a of the pushbutton 32 and is retained by a retainer 112a of the head cap 112 for maintaining the pushbutton 32 biased by the spring as described above at a pre-set position.

With the present dental handpiece 30, when the pushbutton 32 is thrust downwards, the balls 35b rotatably held by the outer race 35c are contacted with the contact portion 33c provided at an upper end of the collet 33, thereby preventing the component parts from being injured due to mistaken manipulation of the pushbutton 32, as in the case of the previous dental handpiece 10.

The rotatable contact member according to the present invention is not limited to the contact members described in the previous embodiments. That is, the rotatable contact member of any desired construction may be employed provided that it may be rotated in unison with the rotating tool holding means on contact of the rotatable contact member with the rotating tool holding means.

Although the present invention has been described with reference to the preferred embodiments, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A dental handpiece comprising a tool for dental treatment operation, tool holding means for detachably and rotatably holding said tool, said tool holding means having a frusto-conically inclined surface, tool detachment means for abutting against said tool holding means to detach said tool from said tool holding means, and rotatable contact means having a plurality of rotatable contact members capable of being point-contacted with the frusto-conically inclined surface of said tool holding means, said rotatable contact means being rotatable with said tool holding means when contacted with said tool holding means, said rotatable contact means having a holding member for rotatably holding said plurality of rotatable contact members, and said plurality of rotatable contact members being arranged in ring pattern on said holding member.

2. The dental handpiece as claimed in claim 1 wherein said rotatable contact means comprises a ball bearing secured to said tool detachment means, and a rotatable contact member held by said ball bearing.

3. The dental handpiece as claimed in claim 1 wherein said tool holding means comprises a rotatable shaft accommodating therein a collet for detachably holding the dental treatment tool, and ball bearings for rotatably supporting said rotatable shaft.

* * * * *

UNITED STATES PATENT AND TRADEMARK OFFICE
CERTIFICATE OF CORRECTION

PATENT NO. : 5,518,398

DATED : May 21, 1996

INVENTOR(S) : Nakanishi et al.

It is certified that error appears in the above-identified patent and that said Letters Patent is hereby corrected as shown below:

On the title page, item 73, Assignee should read --Nakanishi Dental Mfg. Co., Ltd.,-- rather than "Nakanishi Dental Mgf. Co., Ltd.,"

Signed and Sealed this

Fifth Day of November, 1996

*Attest:*

BRUCE LEHMAN

*Attesting Officer*  *Commissioner of Patents and Trademarks*